United States Patent [19]
Tucker et al.

[11] Patent Number: 5,921,914
[45] Date of Patent: Jul. 13, 1999

[54] DEVICE FOR MAINTAINING AN ERECTION

[75] Inventors: Martin S. Tucker, San Fernando; Fernando C. Lopez, North Hills; Antonio S. Hernandez, Reseda, all of Calif.

[73] Assignee: Topco Sales, Inc., San Fernando, Calif.

[21] Appl. No.: 08/924,839

[22] Filed: Sep. 5, 1997

Related U.S. Application Data

[63] Continuation of application No. 08/690,308, Jul. 30, 1996, Pat. No. 5,713,830.

[51] Int. Cl.$^6$ ........................................................ A61F 5/41
[52] U.S. Cl. ................................................................ 600/38
[58] Field of Search ..................................... 128/842, 844, 128/918; 600/38–41; 604/347–353; 24/115 G

[56] References Cited

U.S. PATENT DOCUMENTS

| | | | |
|---|---|---|---|
| 4,224,933 | 9/1980 | Reiling | 600/39 |
| 5,234,401 | 8/1993 | Yamanaka | 600/38 |
| 5,344,389 | 9/1994 | Walsdorf et al. | 600/41 |
| 5,365,641 | 11/1994 | Watanabe et al. | 24/115 G |
| 5,468,211 | 11/1995 | Welch | 600/38 |

FOREIGN PATENT DOCUMENTS

| | | | |
|---|---|---|---|
| 93/13734 | 7/1993 | WIPO | 128/844 |

*Primary Examiner*—Samuel Gilbert
*Attorney, Agent, or Firm*—Oppenheimer Wolff & Donnelly LLP

[57] ABSTRACT

A device for maintaining an erection of a penis has a flexible cuff around the penis. A line extends around the cuff. The line tightens or loosens the cuff around the penis. A bead, through which the line extends, locks the line so that cuff maintains the line and cuff in the tightened position. The cuff has multiple circumferentially ridges, and the line extend between two adjacent ridges. A bead also locks the line in the tightened position. The cuff provides a seal between the hose of a vacuum device and the penis so that the vacuum can cause an erection. While the vacuum is still applied, the line is tightened to constrict the penis so that the erection is maintained. Once the line is tightened, the vacuum hose can be removed. The user then can engage in sexual intercourse.

2 Claims, 2 Drawing Sheets

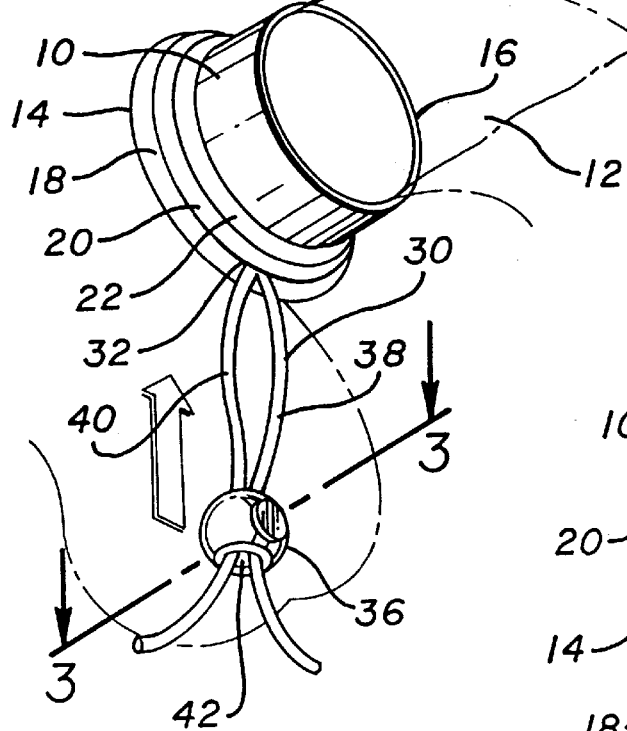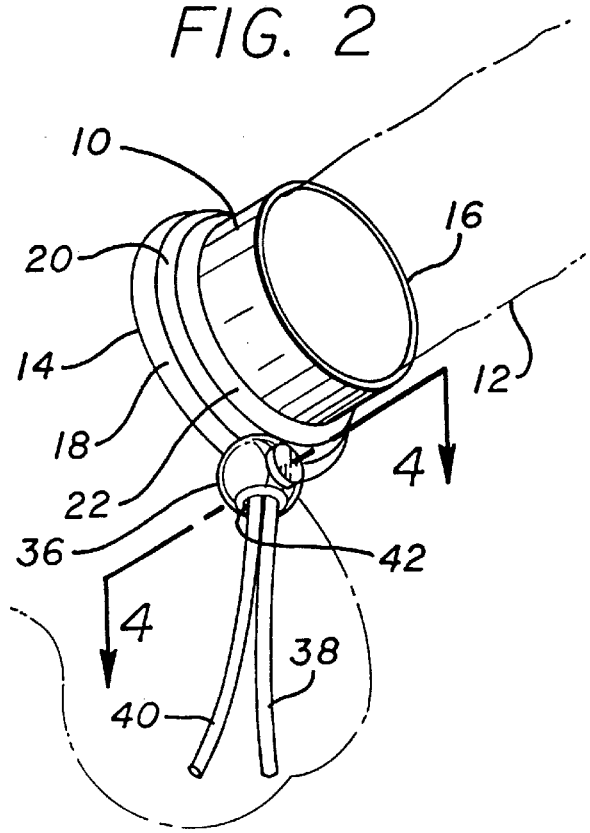

DEVICE FOR MAINTAINING AN ERECTION

This application is a continuation of U.S. application Ser. No. 08/690,308, filed Jul. 30, 1996 now U.S. Pat. No. 5,713,830.

BACKGROUND OF THE INVENTION

1. Field of the Invention

Vacuum pumps promote erections, but when the pump is removed, the erection is minimized instantly, and subsequent coitus is difficult to achieve. The device in this invention is designed primarily, but not solely, to be used with any vacuum device. While the vacuum is in place with the device of this invention, pressure can be applied to the base of the penis without disturbing the vacuum seal. This permits an erection to result even after the vacuum is removed. Once pressure is applied to the penis, premature ejaculation is significantly inhibited. If a man can achieve an erection without a vacuum pump, the device in this invention also will definitely maintain that erection, and it will inhibit premature ejaculation.

2. State of the Art

Impotency, the inability to have or maintain an erection, is a common problem. The problem may be psychological or physically induced and may be the result of injury or disease. Diabetes is a frequent cause. Many medications used to treat unrelated conditions also lead to impotency. Additionally, excessive use of alcohol or illicite drugs can cause temporary or permanent impotency.

Impotency is a problem because it prevents men from engaging in sexual intercourse or other sexual activities. That is very troubling to many men or to their partners. Accordingly, many men seek cures for impotency or devices that allow men to have sexual intercourse despite their inability to have a "natural" erection.

Many devices claim to allow men to have and maintain an erection. For example, it is known that applying a vacuum to the penis can cause an erection. A man normally has an erection when blood flow into the tissues in the penis causes the penis to swell and become erect. It is believed that the vacuum causes a sufficient pressure differential that blood flows into the penis tissues. Because the vacuum device must be placed over the penis to work, it must be removed before intercourse begins. Unfortunately, once the man stops applying a vacuum, the blood flows out of the penis. Therefore, he normally looses his erection quickly—usually too quickly to have satisfying sex.

Heretofore, all vacuum devices were unable to permit the erection achieved during vacuum application to be maintained. Many manufacturers have and do make devices that are placed onto the penis once the vacuum tube is removed. However, during the time it takes to put the device in place, erections instantly begin to dwindle. The present invention relates to a device that applies constriction to an erect penis whether it is erect due to a vacuum system or simply erect without the aid of any external device. Therefore, a man can maintain a constant erection to enable satisfying coitus.

Also, many men who can maintain an erection suffer from premature ejaculation. This condition is a male's inability to control ejaculation or orgasm. One treatment for premature ejaculation is to apply tight constriction to the erect penis. The constriction can prevent ejaculation.

Premature ejaculation also can be controlled by training. One training exercise is to allow the man to become aroused. If the penis is constricted as arousal increases until just before a man begins reaching orgasm, the man can fall to a lower level of arousal and not ejaculate. By repeating the process—heightened arousal and then constriction, the man maintains his erection longer. As the process is repeated over several weeks or months, a man can be trained to postpone ejaculation without constriction.

Again, many constricting devices are available. They include solid metal or plastic rings. Some provide adjustability through a tightening mechanism.

SUMMARY OF THE INVENTION

The principal objects of the present invention are to disclose and provide a device for maintaining an erection or to prevent premature ejaculation. Most importantly, the invention provides a strong seal between a vacuum pump or hose so that a strong vacuum can be applied to the penis. Then, while the device is still in place and the vacuum is still applied, the device can apply constriction to the penis. Therefore, the device maintains the erection.

The device is low cost or construction and is made of plastic parts that can be washed thoroughly.

The device for maintaining an erection of a penis and preventing premature ejaculation of the present invention comprises a flexible cuff. The cuff may be closed into an annulus or it may be partially open. Its flexibility allows the device to act as a seal for a vacuum tube or pump. The device may also have external ridges for engaging the vacuum device. A line is attached to and extends around at least a portion of the cuff. While the vacuum is still applied to the penis, the line is pulled to tighten the cuff around the penis. A lock secures the line so that the cuff remains tight. The line constricts the penis so that after the vacuum hose is removed, the penis remains erect. Accordingly, the man using the present invention can have satisfying coitus.

These and other objects of the invention may be seen more clearly from the detailed description of the preferred embodiment that follows.

BRIEF DESCRIPTION OF THE DRAWINGS

FIG. 1 is a perspective view of the device for maintaining an erection of the present invention in the loose or released position on a penis.

FIG. 2 is a perspective view of the device for maintaining an erection of the present invention in the tightened or closed position shown on a penis.

DETAILED DESCRIPTION OF THE PREFERRED EMBODIMENTS

Figure 3:
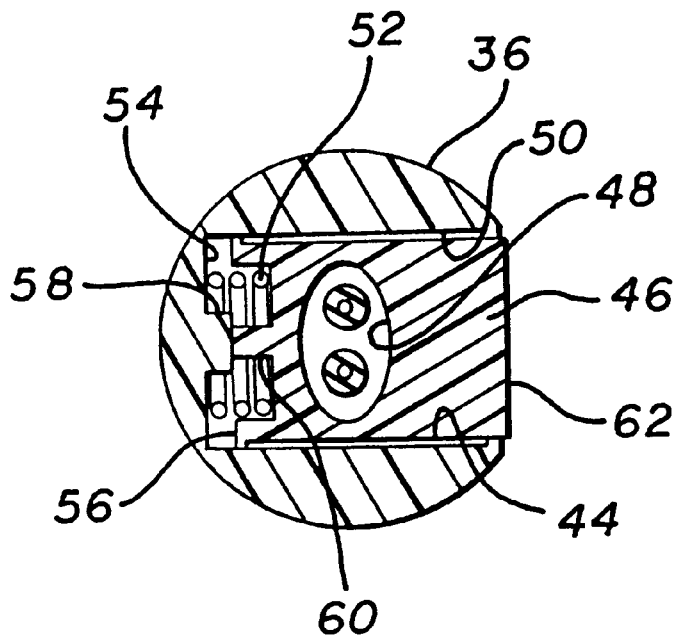
FIG. 3 is a sectional view of a lock used to maintain the present invention in the closed position. The figure is taken through plane 3—3 in FIG. 1, and the lock is open.

The device for maintaining an erection of a penis and controlling premature ejaculation comprising a flexible cuff. In the exemplary embodiment, the cuff 10 is formed of rubber or a rubber-like plastic. It is flexible to conform to the outside of penis 12 (FIGS. 1 and 2). The exemplary embodiment shows the cuff to be a continuous annular cuff, but it could have a side opening. The inside diameter is slightly tapered inward from the proximal end 14 to the distal end 16. The taper does not have to be constant.

Cuff 10 has several annular ribs 18, 20 and 22. They may all be the same diameter, but the exemplary embodiment shows that the proximal rib 18 has a larger diameter than the more distal ribs 20 and 22. The ribs are soft and flexible and are formed as folds during the device's molding process.

The cuff and its ribs are designed to create a seal to a hose of a vacuum pump. The ribs accommodate hoses of different diameters, and the flexible nature of the cuff blocks air flow into the vacuum hose.

A line is attached to and extending around at least a portion of the cuff. In the exemplary embodiment, line 30 (FIGS. 1 and 2) is held between ribs 18 and 20. The line exits between the ribs at a small space 32. So that the line remains inside the ribs 18 and 20, the two ribs are fastened together with adhesive. The line is a flexible plastic material. In the exemplary embodiment, the line is hollow to make it more flexible.

The line causes the cuff to be between a tightened position tightening the cuff around the penis and a loose position loosening the cuff around the penis. FIG. 1 shows the loose position. The line extends through a bead 36. As FIGS. 1 and 2 show, the two ends 38 and 40 of the line pass through the bead.

Figure 4:
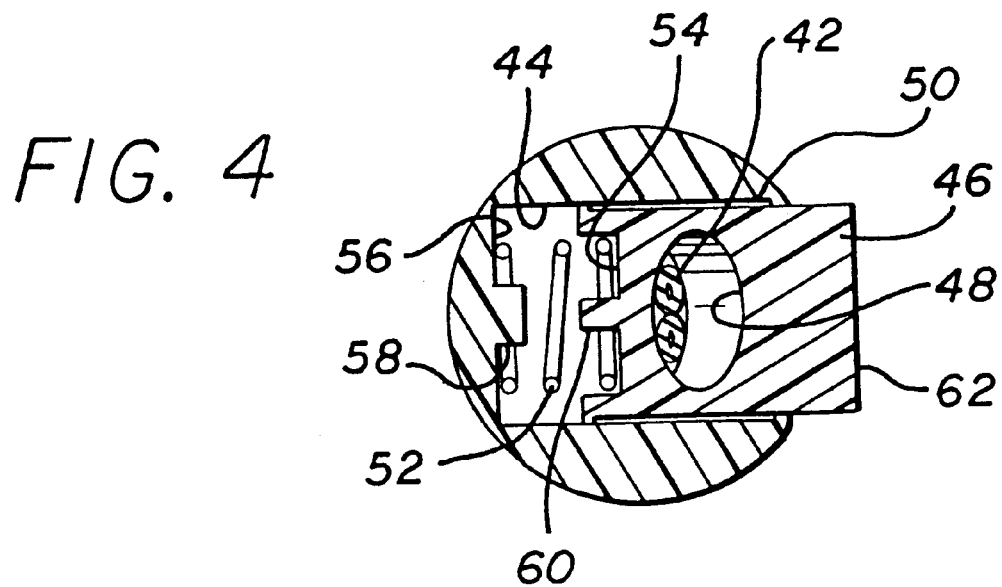
FIG. 4 is a sectional view of the lock and is taken through plane 4—4 in FIG. 2, and the lock is closed.

When one slides the bead toward the cuff (FIG. 2) and pulls on ends 38 and 40 of the line, the line and bead constrict the cuff and the penis. The bead has a lock securing the bead when the line and cuff are in the tightened position. Bead 36 has a line receiving opening extending through the bead. In the exemplary embodiment, line receiving opening 42 is elliptical (FIGS. 1 through 4), it may be circular or rectangular. The bead also has a plunger opening 44, which intersects the line receiving opening (FIGS. 3 and 4). The exemplary embodiment's plunger opening is cylindrical, and a corresponding plunger 46 slides longitudinally in the plunger opening.

FIGS. 3 and 4 show the two extreme positions of the plunger. The plunger and the plunger opening may have projections or grooves to prevent the plunger from falling out of the plunger opening. FIGS. 3 and 4 show one such projection 50.

The plunger 46 has a plunger line opening 48. The opening also is elliptical as FIGS. 3 and 4 show. Its shape conforms to the shape of the line receiving opening 42. As the plunger moves, it positions the plunger line opening between two positions. In its open position (FIG. 3), the plunger line opening 48 is aligned with the line receiving opening 42. In the locked position (FIG. 4), the plunger line opening is out of alignment with the line receiving opening. In the open position, neither the plunger line opening 48 nor the line receiving opening 42 pinch the line 38 and 40. Therefore, the bead can slide along the line. In the locked position, the plunger line opening and the line receiving opening pinch the line to prevent the bed from sliding along the line. Thus, when the plunger is in its locked position (FIG. 4), the bead secures the line tightly.

A spring 52 biases the plunger outward to the locked position (FIG. 4). As FIGS. 3 and 4 show, compression spring 52 extends between wall 54 of the bead and wall 56 of the plunger. Both walls may have a groove 58 and 60 to receive the respective ends of the spring and maintain the spring's alignment.

As FIG. 4 shows, when the bead is in the locked position, part of the plunger projects from the bead. To unlock the line, the user pushes the plunger against the spring bias until the plunger's end 62 is about flush with the outside of the bead (FIG. 3). It is in that position that the bead can move along the line.

If one is using the present invention for impotency, one installs cuff 10 along the base of the penis 12. With the line 30 still loose (FIG. 1), suction is applied to the entire penis. To do this, the penis is inserted into a suction hose, and the end of the hose is pushed against one of the ribs 18, 20 or 22. The flexible rib helps maintain reduced pressure around the penis. The user may also engage in other arousing activities. Once he attains an erection, the user tightens the line 30 by pushing bead 36 tightly against the cuff to constrict the base of the penis. It is important to note that the vacuum is maintained while the line is being tightened. The invention's design is such that the man or his partner can reach the line and tighten it without disturbing the vacuum seal between the hose and cuff 10. Therefore, the man maintains his erection while the line is tightened. The vacuum then is released. Because the line is tight and constricting the penis, the erection is maintained. The man can engage in sexual activity. When he finishes, he releases the bead, loosens the line and removes the device.

One can use the present invention in different ways to prevent premature ejaculation. First, it will control premature ejaculation for one using vacuum to achieve an erection. That is, the line 30 can be tight enough to stop ejaculation.

The device also can be used for men who can achieve an erection without a vacuum. For example, one would install cuff 10 along the base of the penis 12. As the man become more aroused, he or his partner tightens the line by pushing bead 36 tightly against the cuff to constrict the base of the penis. This action slows down arousal. After sufficient loss of arousal, the man starts arousing activity again. Once the man is sufficiently aroused, he or his partner again constricts the base of the penis by tightening the line. This action may be repeated several times. Alternatively, the man may allow normal arousal to continue. He tightens the line and cuff but continues sexual activity and uses the tight line to prevent ejaculation.

Numerous modifications and alternate embodiments will occur to those skilled in the art. Therefore, applicant intends that the invention be limited only in terms of the appended claims.

We claim:

1. An apparatus for maintaining an erection, comprising:

a flexible cuff;

a tightening device comprising a line attached to and extending around a portion of the cuff, associated with the flexible cuff, adapted to selectively place the flexible cuff in a tightened orientation around the base of a penis and a loosened orientation; and sealing means associated with the flexible cuff for receiving a vacuum device and creating a seal between the vacuum device and the flexible cuff.

2. An apparatus for maintaining an erection, comprising:

a flexible cuff;

a tightening device, associated with the flexible cuff, adapted to selectively place the flexible cuff in a tightened orientation around the base of a penis and a loosened orientation; and at least two annular ribs extending around the flexible cuff for receiving a vacuum device and creating a seal between the vacuum device and the flexible cuff.

* * * * *